(12) United States Patent
Jolidon et al.

(10) Patent No.: US 7,253,318 B2
(45) Date of Patent: Aug. 7, 2007

(54) BENZYLOXY DERIVATIVES AS MAOB INHIBITORS

(75) Inventors: Synese Jolidon, Blauen (CH); Rosa Maria Rodriguez-Sarmiento, Basel (CH); Andrew William Thomas, Birsfelden (CH); Wolfgang Wostl, Grenzach-Wyhlen (DE); Rene Wyler, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 68 days.

(21) Appl. No.: 11/156,417

(22) Filed: Jun. 20, 2005

(65) Prior Publication Data
US 2005/0288367 A1 Dec. 29, 2005

(30) Foreign Application Priority Data
Jun. 23, 2004 (EP) .................. 04102907

(51) Int. Cl.
*C07C 233/65* (2006.01)
*A61K 31/165* (2006.01)

(52) U.S. Cl. .................. 564/171; 564/175; 560/32; 558/414; 514/478; 514/520; 514/617

(58) Field of Classification Search ............. 514/478, 514/520, 617; 564/171, 175; 560/32; 558/414
See application file for complete search history.

(56) References Cited

U.S. PATENT DOCUMENTS 4,777,280 A 10/1988 Eidman et al.

FOREIGN PATENT DOCUMENTS

| JP | 58-32859 | * | 2/1983 |
| WO | WO 96/40095 | | 12/1996 |
| WO | WO 97/33572 | | 9/1997 |
| WO | WO 01/34172 | | 5/2001 |
| WO | WO 2004/033422 A2 | | 4/2004 |

OTHER PUBLICATIONS

Tarzia et al, J. Med. Chem., vol. 46, 2352-2360, 2003.*
Bach et al., Proc. Natl. Acad. Sci. vol. 85: pp. 4934-4938 (1988).
Cesura & Pletscher, Prog. Drug Research vol. 38: pp. 171-297 (1992).
Fowler et al., J. Neural. Transm. vol. 49: pp. 1-20 (1980).
Benedetti et al., Biochem. Pharmacol. vol. 38: pp. 555-561 (1989).
Saura et al., Neuroscience vol. 70: pp. 755-774 (1996).
Bentué-Ferrer et al., CNS Drugs vol. 6: pp. 217-236 (1996).
Gardner et al. J. Clin. Psychiatry vol. 57: pp. 99-104 (1996).
Schlaeger & Christensen, Cytotechnology vol. 30: pp. 71-83 (1999).
Zhou & Panchuk-Voloshina, Analytical Biochemistry vol. 253: pp. 169-174 (1997).
Chemical abstract No. 1999:698108, XP002356168 & JP 11 302235 A2.
Chemical abstract No. 1999:350535, XP002356169 & JP 11 47881 A2.
Paolo Pevarello, et al., Journal of Medicinal Chemistry, vol. 41(4), pp. 579-590 (1998).
David M. Walba, et al., Journal of Organic Chemistry, vol. 54(20), pp. 4939-4943 (1989).
Mitsuyo Tanaka, et al., Chemical & Pharmaceutical Bulletin, vol. 33(6), pp. 2403-2410 (1985).
R.L. Metcalf, et al., Journal of Agricultural and Food Chemistry, vol. 15(6), pp. 1022-1029 (1967).
Chemical abstract No. 1975:31085, XP002356170 & Yakugaku Zasshi, vol. 94(9), pp. 1061-1069 (1974), ISSN: 0031-6903.

* cited by examiner

*Primary Examiner*—Shailendra Kumar
(74) *Attorney, Agent, or Firm*—George W. Johnston; Patricia S. Rocha-Tramaloni; Kimberly J. Prior

(57) ABSTRACT

The invention relates to compounds of the formula

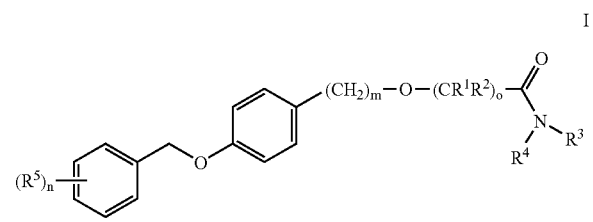

and their pharmaceutically acceptable salts wherein
$R^1$, $R^2$, $R^3$, $R^4$, $R^5$,
n, m, and o are as defined in the specification. The compounds are selective monoamine oxidase β inhibitors and are useful for the treatment and prevention of Alzheimer's disease and senile dementia, as well as other CNS disorders. The invention also relates to processes for preparing such compounds and pharmaceutical compositions containing them.

17 Claims, No Drawings

BENZYLOXY DERIVATIVES AS MAOB INHIBITORS

BACKGROUND OF THE INVENTION

Monoamine oxidase (MAO) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes (A. W. Bach et al., *Proc. Natl. Acad. Sci. USA* 1988, 85, 4934-4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, Prog. Drug Research 1992, 38, 171-297). Brain MAO-B activity appears to increase with age. This increase has been attributed to the gliosis associated with aging (C. J. Fowler et al., *J. Neural. Transm.* 1980, 49, 1-20). Additionally, MAO-B activity is significantly higher in the brains of patients with Alzheimer's disease (P. Dostert et al., *Biochem. Pharmacol.* 1989, 38, 555-561) and it has been found to be highly expressed in astrocytes around senile plaques (Saura et al., *Neuroscience* 1994, 70, 755-774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in *CNS Drugs* 1996, 6, 217-236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99-104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The invention provides benzyloxy derivatives of the formula I

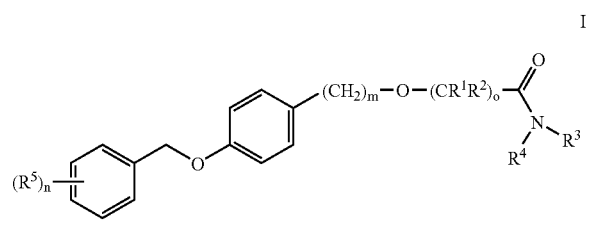

wherein $R^1$ and $R^2$ are each independently hydrogen or $C_1$-$C_6$-alkyl;

$R^3$ and $R^4$ are each independently hydrogen or $C_1$-$C_6$-alkyl;

$R^5$ is halogen, CN, ($C_1$-$C_6$)-alkyl or ($C_1$-$C_6$)-alkoxy; and n, m and o are each independently 0, 1 or 2;

and pharmaceutically acceptable salts thereof.

The invention includes individual isomers of the compounds of formula I as well as racemic and non-racemic mixtures thereof.

The invention also provides methods for the manufacture of compounds of formula I and their pharmaceutically acceptable salts.

Compounds of formula I and their pharmaceutically acceptable salts, as individual isomers of the compounds of formula I as well as racemic and non-racemic mixtures thereof (hereinafter: Pharmaceutical Compound) have pharmacological activity and are useful as pharmaceuticals. Thus, the invention also provides pharmaceutical compositions comprising a therapeutically effective amount of a Pharmaceutical Compound and a pharmaceutically acceptable excipient. The invention further provides methods for the production of such pharmaceutical compositions.

In particular, Pharmaceutical Compounds inhibit the activity of monoamine oxidase B. As such, Pharmaceutical Compounds are useful as selective inhibitors of monoamine oxidase B, e.g. in the treatment or prevention of diseases and conditions in which activity of monoamine oxidase B plays a role or is implicated. Such conditions include in particular acute and/or chronic neurological disorders.

Acute and/or chronic neurological disorders include psychosis, schizophrenia, Alzheimer's disease, cognitive disorders and memory deficits like mild cognitive impairment, age-related cognitive decline, vascular dementia, Parkinsons's disease, memory impairment associated with depression or anxiety, Down's syndrome, stroke, traumatic brain injury, and attention deficit disorder. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychotic episodes, opiate addiction, anxiety, vomiting, dyskinesia and depression.

Thus, the invention further provides methods for the treatment of diseases in which monoamine oxidase B is implicated, such as those described above. In one embodiment, the acute and/or chronic neurological disorder is Alzheimer's disease. In another embodiment, the acute and/or chronic neurological disorder is mild cognitive impairment or senile dementia.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The terms "$C_1$-$C_6$-alkyl" and "lower alkyl" used in the present application denote straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

The term "halogen" denotes fluorine, chlorine, bromine and iodine.

"Alkoxy" or "($C_1$-$C_6$)-alkoxy" means the residue —O—R, wherein R is a lower alkyl residue as defined herein. Examples of alkoxy radicals include, but are not limited to, methoxy, ethoxy, isopropoxy, and the like.

"Pharmaceutically acceptable salts" of a compound means salts that are pharmaceutically acceptable, which are generally safe, non-toxic, and neither biologically nor otherwise undesirable, and that possess the desired pharmacological activity of the parent compound.

These salts are derived from an inorganic or organic acid or base.

Such salts include:
(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric add, ethanesulfonic acid, fumaric acid, glucoheptonic add, gluconic acid, glutamic add, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic add, dibenzoyl-L-tartaric acid, tartaric acid, p-toluene-sulfonic acid, trimethylacetic acid, 2,2,2-trifluoroacetic acid, and the like; or
(2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

"Pharmaceutically acceptable" such as pharmaceutically acceptable carrier, excipient, etc., means pharmacologically acceptable and substantially non-toxic to the subject to which the particular compound is administered.

"Therapeutically effective amount" means an amount that is effective to prevent, alleviate or ameliorate symptoms of disease or prolong the survival of the subject being treated.

Furthermore, as used herein, a mammal in need of treatment of an acute and/or chronic neurological disorder means a mammal, e.g. a human, that is suffering from, or is at risk of suffering from, an acute and/or chronic neurological disorder. Term "patient" and "human" are used interchangeably herein.

As used herein, the terms "treat", "treating" and "treatment", and the like, as applied to an acute and/or chronic neurological disorder, refer to methods that slow, ameliorate, reduce or reverse such a disorder or any symptoms associated with said disorder, as currently afflicting the subject, as well as methods that prevent such a disorder or any symptoms thereof, from occurring The invention provides benzyloxy derivatives of the formula I

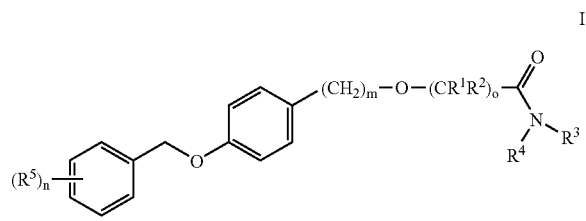

wherein $R^1$ and $R^2$ are each independently hydrogen or $C_1$-$C_6$-alkyl;

$R^3$ and $R^4$ are each independently hydrogen or $C_1$-$C_6$-alkyl;

$R^5$ is halogen, CN, ($C_1$-$C_6$)-alkyl or ($C_1$-$C_6$)-alkoxy; and n, m and o are each independently 0, 1 or 2;

and pharmaceutically acceptable salts thereof.

Among compounds of the present invention certain compounds of formula I, or pharmaceutically acceptable salts thereof, are preferred Preferred compounds of formula I are those, in which o is 1 and m is 0, for example the following compounds:

2-(4-benzyloxy-phenoxy)-N-methyl-acetamide,

2-[4-(4-cyano-benzyloxy)-phenoxy]-N-methyl-acetamide,

2-[4-(4-chloro-benzyloxy)-phenoxy]-N-methyl-acetamide,

2-[4-(2-fluoro-benzyloxy)-phenoxy]-N-methyl-acetamide,

2-[4-(3-fluoro-benzyloxy)-phenoxy]-N-methyl-acetamide,

2-[4-(4-fluoro-benzyloxy)-phenoxy]-N-methyl-acetamide, (RS)-2-[4-(3-fluoro-benzyloxy)-phenoxy]-N-methyl-propionamide (RS)-2-[4-(3-chloro-benzyloxy)-phenoxy]-N-methyl-propionamide (S or R)-2-[4-(3-chloro-benzyloxy)-phenoxy]-N-methyl-propionamide, (RS)-2-[4-(4-cyano-benzyloxy)-phenoxy]-N-methyl-propionamide, (RS)-2-[4-(3-fluoro-benzyloxy)-phenoxy]-N-methyl-butyramide, (RS)-2-[4-(3-chloro-benzyloxy)-phenoxy]-N-methyl-butyramide or (RS)-2-[4-(4-cyano-benzyloxy)-phenoxy]-N-methyl-butyramide.

Preferred are further compounds of formula I, in which o is 2 and m is 0, for example 3-[4-(3-fluoro-benzyloxy)-phenoxy]-propionamide.

A further preferred group of compounds of formula I are those, wherein o is 0 and m is 2, for example carbamic acid 2-[4-(3-fluoro-benzyloxy)-phenyl]-ethyl ester.

Preferred are also compounds of formula I, wherein o is 0 and m is 1, for example methyl-carbamic acid 4-(3-fluoro-benzyloxy)-benzyl ester.

A further preferred group of compounds of formula I are those, wherein o is 1 and m is 1, for example 2-[4-(3-fluoro-benzyloxy)-benzyloxy]-acetamide.

Also preferred are compounds in which n is 1.

Another preferred group of compounds are those in which both $R^1$ and $R^2$ are hydrogen.

Compounds in which $R^1$ is $C_1$-$C_6$-alkyl, in particular compounds in which $R^1$ is methyl or ethyl also are preferred. Also preferred within this group of compounds are those compounds in which $R^2$ is hydrogen.

Another preferred group of compounds are those in which $R^1$ and $R^2$ are each independently $C_1$-$C_6$-alkyl.

The present compounds of formula I and their pharmaceutically acceptable salts can be manufactured by methods known in the art, for example by processes described below, which processes comprise a) reacting a compound of formula

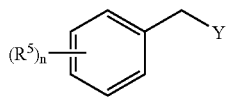

II with a compound of formula

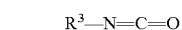

III wherein Y is a leaving group, to obtain a compound of formula

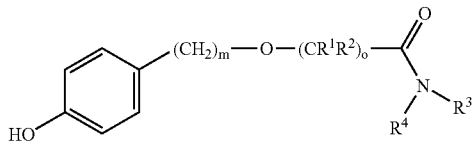

I wherein the substituents are as described above, or b) reacting a compound of formula

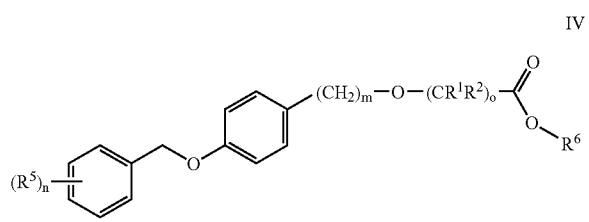

IV wherein $R^6$ is $C_1$-$C_6$-alkyl, with an amine of formula

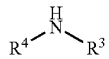

V to obtain a compound of formula

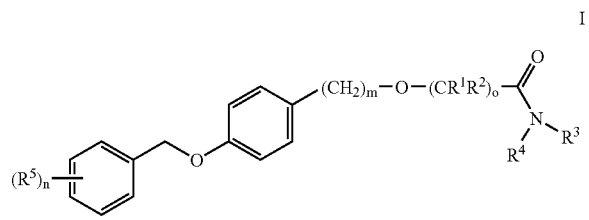

I wherein the substituents are as described above, or c) reacting a compound of formula

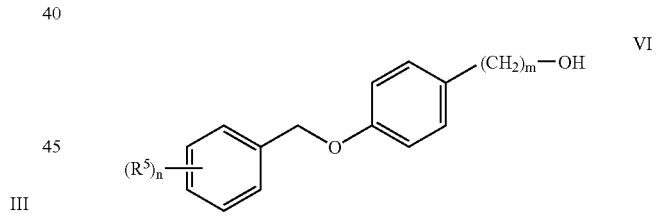

VI with KOCN or with $R^3$—N=C=O    VII to obtain a compound of formula

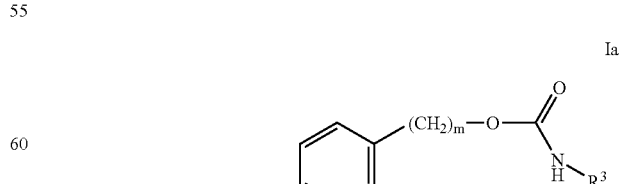

Ia wherein the substituents are as described above, or d) reacting a compound of formula

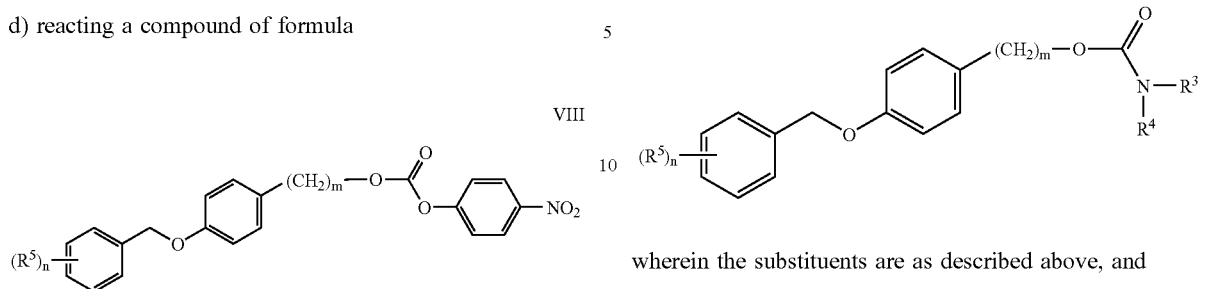

with a compound of formula HNR³R⁴ V
to obtain a compound of formula

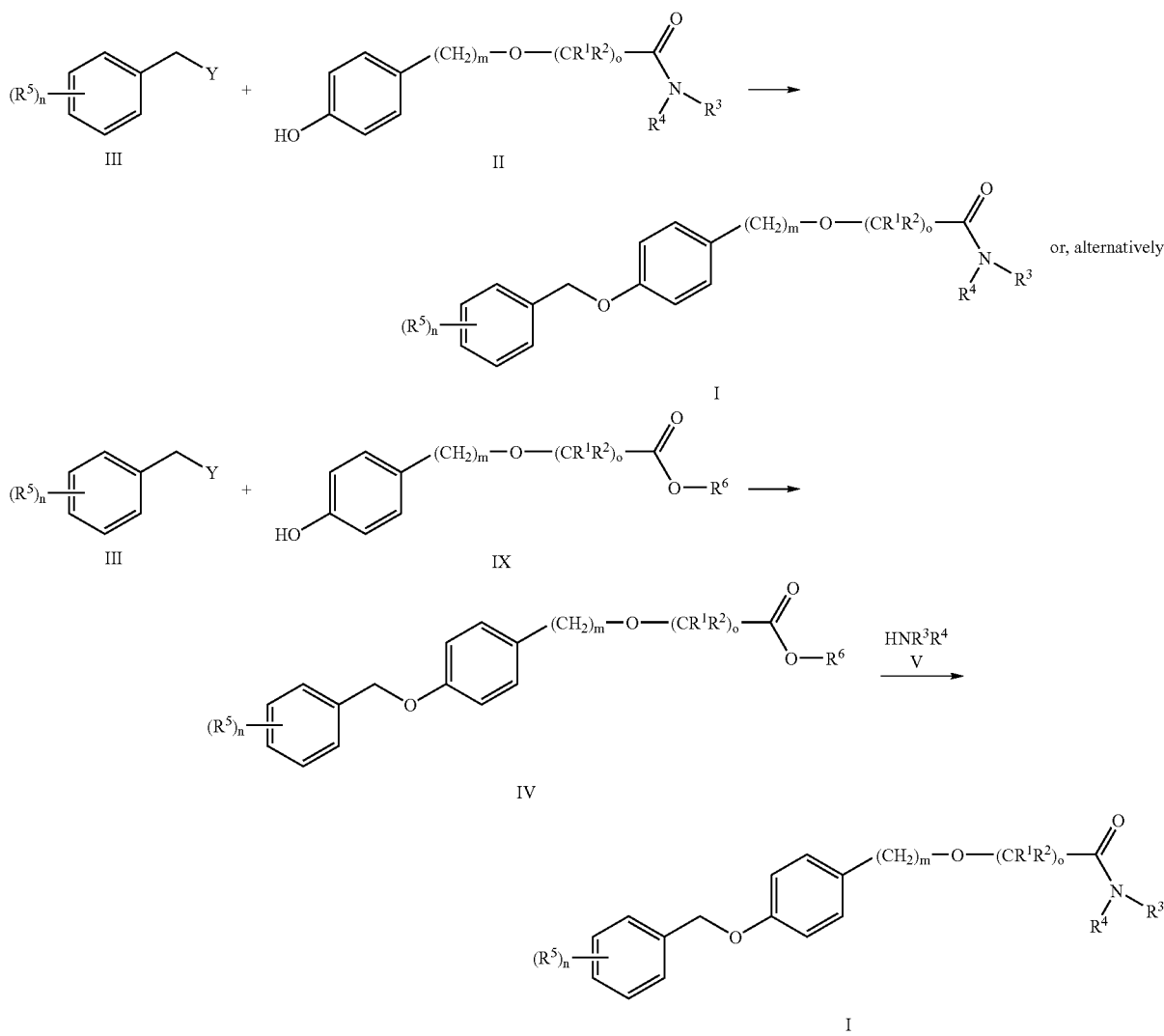

wherein the substituents are as described above, and
if desired, converting the compounds obtained into pharmaceutically acceptable acid addition salts.

In accordance with the present invention, the compounds of formula I can be prepared by the methods shown in schemes 1 to 3. The starting materials of formulas III, V, XII and XV are commercial available or may be prepared by methods known in the art.

The substituents, n, m and o have the meaning as described above and Y is a leaving group, such as halogen, a toluenesulfonyl group, a methanesulfonyl group or a trifluoromethanesulfonyl group.

Compounds of formula I can be formed by Williamson's ether synthesis, starting from the corresponding p-substituted phenols of formula II by reaction with benzylic halides, tosylates, mesylates or triflates of formula III. Compounds of formula III are commercial available or may be prepared by methods known in the art. Bases used can be for example alcoholates or carbonates (sodium, potassium or cesium carbonate). Preferred solvents are lower alcohols, acetonitrile or lower ketones at temperatures between 20° C. and reflux temperature. Another approach is the Mitsunobu-coupling of benzylic alcohols of formula III with the corresponding phenols of formula IX. Usually, the reaction is done in inert solvents like, for example, diethyl ether or tetrahydrofurane, using dialkyl-azo-dicarboxylates in presence of phosphines (for example tributyl- or triphenyl-phosphine). The ester of formula IV can be transformed into the desired final product of formula I using standard procedures: by aminolysis with $HNR^3R^4$ (V) in solvents like methanol, tetrahydrofurane etc., or by saponification to the corresponding acid (for example by LiOH or KOH in methanol), activation of the acid via the acid chloride (thionyl chloride or oxalyl chloride) or activation by N,N'-dicyclohexylcarbodiimide (DCC), N-(3-dimethylamino-propyl)-N'-ethyl-carbodiimide hydrochloride (EDC) etc. and coupling with the amine $HNR^3R^4$.

Compounds of formula IX can be obtained by using a compound of formula IV, which may be prepared in accordance with Scheme 2, with an optionally substituted benzyl residue which can function as a transient group that can be cleaved by hydrogenolysis. The resulting phenols of formula IX can then be re-alkylated by a different benzyl group under the aforementioned conditions. As known to those skilled in the art, this process is only possible on condition that the other substituents and functionalities are stable under the aforementioned reaction conditions for the hydrogenolysis and alkylation reaction.

A method for preparing intermediates for compounds of formula I is shown in scheme 2. In close analogy to the procedures described before, the mono-alkylation of phenol X by Williamson's ether synthesis by reaction with benzylic halides, tosylates, mesylates or triflates of formula III yields hydroxy derivatives of formula VI. An alternative approach is the Mitsunobu-coupling of benzylic alcohols of formula III with the corresponding phenols of formula X. Usually, the reaction is done in inert solvents, for example, diethyl ether or tetrahydrofurane, using dialkyl-azo-dicarboxylates in presence of phosphines (for example tributyl- or triphenyl-phosphine). Compounds of formula VI can be further alkylated by ester derivatives of formula XII to yield compounds of formula IV. Also for this alkylation reaction, conditions can be applied already described before and, basically, known to those skilled in the art.

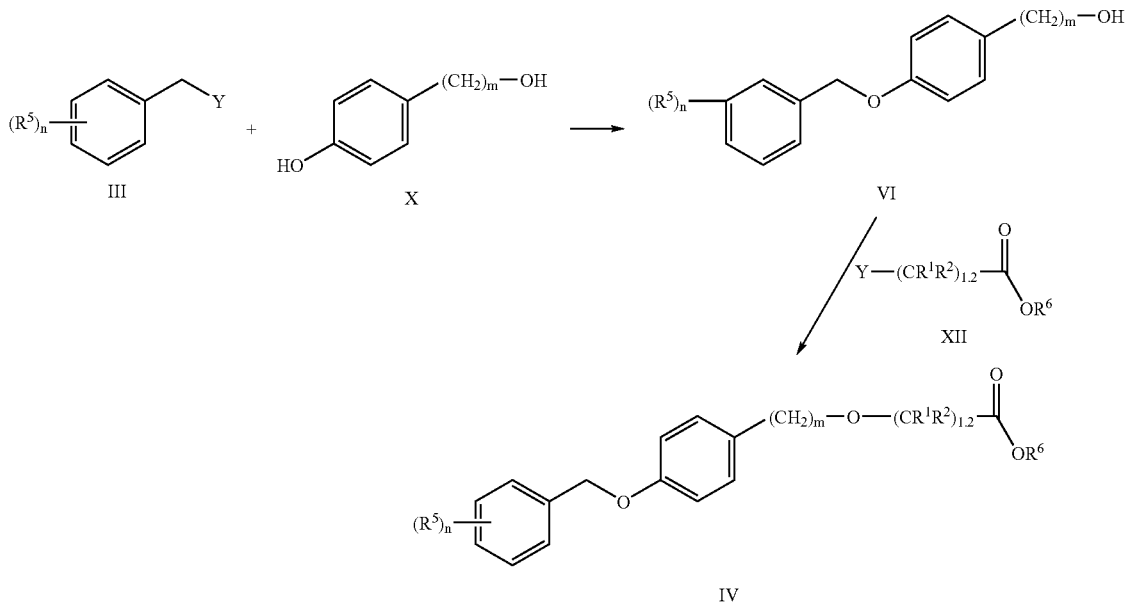

Scheme 2

The substituents, n and m have the meaning as described above.

The preparation of compounds of formula Ia and Ib, wherein n=0, is shown in scheme 3. The reaction of hydroxy derivatives of formula VI with potassium cyanate or alkyl isocyanates (VII) in sealed vessels using solvents like dichloromethane or toluene at a temperature between room temperature and 100° C. yields the carbamates of formula Ia.

The reaction of hydroxy derivatives of formula VI with phenyl chloroformates (XV), preferably substituted phenyl chloroformates, e.g. 4-nitrophenyl chloroformates, yields carbonates of formula VIII. Treatment of those carbonates with amines of formula V, preferably conducted in sealed tubes, and in solvents inert under the reaction conditions like e.g. tetrahydrofurane or dioxane at temperatures between 0 and 60° C. yields compounds of formula Ib.

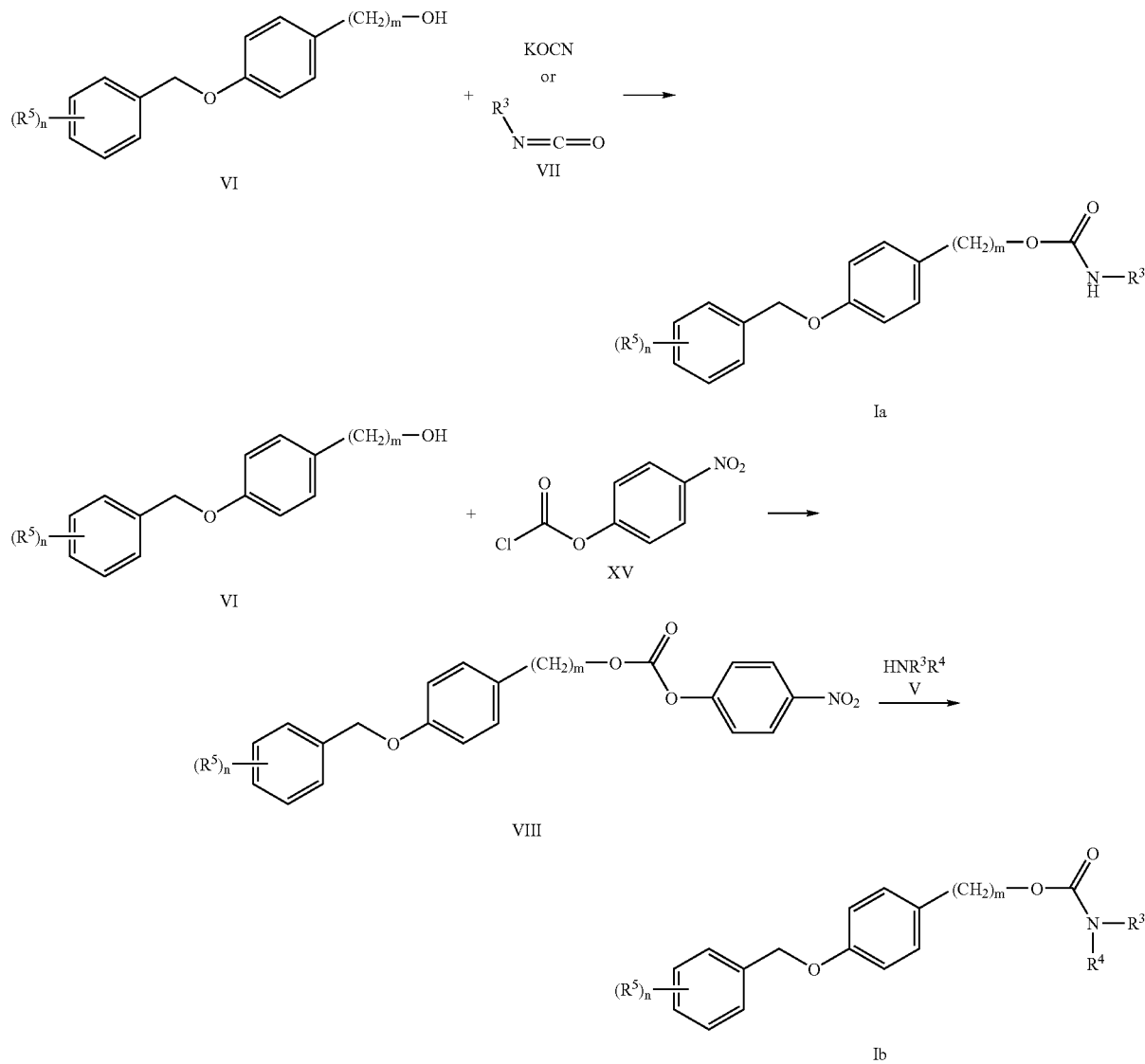

Scheme 3

The substituents, n and m have the meaning as described above.

Compounds of formula I can also exist in optically pure form. Separation into antipodes can be affected according to methods known per se, either at an early stage of the synthesis or by separation of enantiomers of formula I. At an early stage, separation can be effected starting with compounds of formula XII by salt formation with an optically active amine such as, for example, (+)- or (−)-1-phenylethylamine or (+)- or (−)-1-naphthylethylamine and separation of the diastereomeric salts by fractional crystallisation or by derivatisation with a chiral auxiliary substance such as, for example, (+)- or (−)-2-butanol, (+)- or (−)-1-phenylethanol, or (+)- or (−)-menthol followed by separation of the diastereomeric products by chromatography and/or crystallisation and subsequent cleavage of the bond to the chiral auxiliary substance. Alternatively, separation of the enantiomers of formula I can be effected by chromatography on a chiral phase. Furthermore, compounds of formula I can also be obtained from enantiopure intermediates obtained by biotransformation, e.g. by hydrolysis of esters of formula IV, IX, XII, or XIV, by enzymes, such hydrolases or lipases. In order to determine the absolute configuration of the derivatives obtained, the pure diastereomeric salts or derivatives can be analyzed by conventional spectroscopic methods, with X-ray spectroscopy on single crystals being an especially suitable method.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, monoamine oxidase B inhibitors and can be used for the treatment or prevention of diseases in which MAO-B inhibitors are beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (G. M. Sullivan, International patent application No. WO 01/34172 A2), peripheral neuropathy caused by cancer chemotherapy (G. Bobotas, International Patent Application No. WO 97/33572 A1), or the treatment of multiple sclerosis (R. Y. Harris, International patent application No. WO 96/40095 A1) and other neuroinflammatory diseases.

The pharmacological activity of Pharmaceutical Compounds was tested using the following method:

The cDNA's encoding human MAO-A and MAO-B were transiently transfected into EBNA cells using the procedure described by Schlaeger and Christensen [Cytotechnology 15:1-13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169-174 (1997)]. Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 µM N-acetyl-3,7,-dihydroxyphenoxazine (Amplex Red, Molecular Probes). The samples were further incubated for 30 min at 37° C. in a final volume of 200 µl and absorbance was then determined at a wavelength of 570 nm using a SpectraMax plate reader (Molecular Devices). Background (non-specific) absorbance was determined in the presence of 10 µM clorgyline for MAO-A or 10 µM L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of compounds of formula I as measured in the assay described above are in the range of 1 µM or less, and ideally 0.1 µM or less. The below table shows exemplary $IC_{50}$ values of compounds of formula I in one of their enantiomeric forms:

| Example | human MAO-B [$IC_{50}$ (µM)] | human MAO-A [$IC_{50}$ (µM)] |
| --- | --- | --- |
| 2 | 0.052 | >10 |
| 3 | 0.028 | 2.86 |
| 4 | 0.012 | 2.44 |
| 5 | 0.081 | >9 |
| 6 | 0.021 | >10 |
| 7 | 0.009 | 5.40 |
| 11 | 0.031 | >10 |
| 12 | 0.015 | >10 |
| 13 | 0.009 | >10 |
| 14 | 0.031 | >10 |
| 17 | 0.056 | >10 |
| 18 | 0.028 | >10 |
| 19 | 0.074 | >10 |
| 23 | 0.044 | >10 |
| 24 | 0.068 | >10 |
| 26 | 0.089 | >10 |
| 27 | 0.051 | >10 |

The present invention also provides pharmaceutical compositions containing Pharmaceutical Compounds and a pharmaceutically acceptable carrier. Such pharmaceutical compositions can be in the form of tablets, coated tablets, dragées, hard and soft gelatin capsules solutions, emulsions or suspensions. The pharmaceutical compositions can also be in the form of suppositories, or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, e.g., as such carriers for tablets, coated tablets, dragées and hard gelatin capsules. Suitable carriers for soft gelatin capsules are, e.g., vegetable oils, waxes, fats, semi-solid and liquid polyols and the like; depending on the nature of the active substance no carriers are, however, usually required in the case of soft gelatin capsules. Suitable carriers for the production of solutions and syrups are, e.g., water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, e.g., natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

The present invention also provides a method for the manufacture of pharmaceutical compositions. Such method includes bringing one or more Pharmaceutical Compounds and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

Pharmaceutical Compounds are selective MAO-β inhibitors. Therefore, the present invention also provides methods of treating diseases that are mediated by monoamine oxidase B. Such methods include administering a therapeutically effective amount of a Pharmaceutical Compound to a patient in need of such treatment. In one embodiment, the invention provides a method for the treatment of Alzheimer's disease. In another embodiment, the invention provides a method of the treatment of senile dementia.

The dosage at which Pharmaceutical Compounds can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided for illustration of the invention. They should not be considered as limiting the scope of the invention, but merely as being representative thereof.

EXAMPLE 1

2-[4-(4-Fluoro-benzyloxy)-phenoxy]-acetamide a) 4-(4-Fluoro-benzyloxy)-phenol

A solution of 10 g of hydroquinone in 90 ml of acetonitrile was treated with 8.58 g of 4-fluorobenzylbromide and 15.7 g of potassium carbonate. The mixture was heated to 90° C. and stirred during 18 h. For the working-up, the reaction mixture was cooled to room temperature and treated with cold water. The solid material that has formed was filtered, washed twice with cold water and dried. For purification and separation from the bis-ether, the crude material was chromatographed on silica gel using a 4:1 mixture of heptane and ethyl acetate as the eluent. There were obtained 4.05 g (27% of theory) of 4-(4-fluoro-benzyloxy)-phenol as a white solid; MS: m/e=218 (M)$^+$.

b) [4-(4-Fluoro-benzyloxy)-phenoxy]-acetic acid ethyl ester

A solution of 3 g of 4-(4-fluoro-benzyloxy)-phenol in 40 ml of 2-butanone was treated with 2.5 g potassium carbonate and 1.6 ml of ethyl bromoacetate. The mixture was stirred at 80° C. during 3 h, then, in order to complete the reaction, 1.7 g of potassium carbonate and 1.9 ml of ethyl bromoacetate were added successively in four portions during a period of 24 h. For the working-up, the reaction mixture was cooled to room temperature, then treated with water and extracted with ethyl acetate. The organic layer was separated, dried over magnesium sulphate and evaporated under reduced pressure. There were obtained 2.95 g (71% of theory) of [4-(4-fluoro-benzyloxy)-phenoxy]-acetic acid ethyl ester as brownish crystals which were pure enough to be used in the next step without further purification; MS: m/e=304 (M)$^+$.

c) 2-[4-(4-Fluoro-benzyloxy)-phenoxy]-acetamide

A solution of 500 mg of [4-(4-fluoro-benzyloxy)-phenoxy]-acetic acid ethyl ester in 10 ml of tetrahydrofurane was treated with 3.3 ml of sodium hydroxide solution (1 N). The mixture was heated at 50° C. for 2 h, then it was cooled to room temperature and 3.3 ml of hydrochloric acid (1 N) were added. While the tetrahydrofurane was evaporated under reduced pressure, the acid precipitated and, thereafter, was collected on a filter funnel. After washing with water and drying under reduced pressure, 376 mg of [4-(4-fluoro-benzyloxy)-phenoxy]-acetic acid was obtained, which was directly used for the further transformation.

The crude acid was dissolved in 5 ml of N,N-dimethylformamide, 293 mg of 1,1'-carbonyl-diimidazole were added and the resulting solution was heated at 50° C. for 1 h. Then the mixture was cooled to room temperature, 0.16 ml of ammonium hydroxide solution (25%) was added and stirring continued at room temperature during 18 h. For the working-up, the reaction mixture was treated with water to precipitate the product, which was collected on a filter funnel and washed with water. After crystallisation from water 337 mg (74% of theory) of 2-[4-(4-fluoro-benzyloxy)-phenoxy]-acetamide were obtained as white solid; MS: m/e=276 (M+H)$^+$.

EXAMPLE 2

2-(4-Benzyloxy-phenoxy)-N-methyl-acetamide a) 4-Benzyloxy-phenol

In analogy to the procedure described in Example 1a), the alkylation of hydroquinone with benzylbromide yielded the 4-benzyloxy-phenol as a colourless solid.

b) (4-Benzyloxy-phenoxy)-acetic acid methyl ester

In analogy to the procedure described in Example 1b), the alkylation of 4-benzyloxy-phenol with methyl bromoacetate using cesium carbonate as the base yielded the (4-benzyloxy-phenoxy)-acetic acid methyl ester as white crystals; MS: m/e=272 (M)$^+$.

c) 2-(4-Benzyloxy-phenoxy)-N-methyl-acetamide

In analogy to the procedure described in Example 1c), the (4-benzyloxy-phenoxy)-acetic acid was reacted with methylamine using 1,1'-carbonyl-diimidazole as the condensation reagent. 2-(4-benzyloxy-phenoxy)-N-methyl-acetamide was obtained as white crystals; MS: m/e=272 (M+H)$^+$.

EXAMPLE 3

2-[4-(4-Cyano-benzyloxy)-phenoxy]-N-methyl-acetamide a) 2-(4-Hydroxy-phenoxy)-N-methyl-acetamide A solution of 4.7 g of 2-(4-benzyloxy-phenoxy)-N-methyl-acetamide [Example 2c)] in 150 ml of tetrahydrofurane was hydrogenated at atmospheric pressure and room temperature using 470 mg of palladium on charcoal (10%) as the catalyst. For the working-up, the reaction mixture was filtered over a Dicalite layer and the resulting solution was evaporated under reduced pressure. The residue was triturated in ether and the solid collected on a filter funnel. After drying there were obtained 2.95 g (93% of theory) of 2-(4-hydroxy-phenoxy)-N-methyl-acetamide as white crystals; MS: m/e=181 (M)$^+$.

b) 2-[4-(4-Cyano-benzyloxy)-phenoxy]-N-methyl-acetamide

A solution of 500 mg of 2-(4-hydroxy-phenoxy)-N-methyl-acetamide in 25 ml of 2-butanone was treated with 762 mg of potassium carbonate and 595 mg of 4-bromomethyl-benzonitrile. The reaction mixture was stirred at room temperature for 60 h. For the working-up, the reaction mixture was treated with water, then extracted with ethyl acetate. The aqueous layer was re-extracted with ethyl acetate, the combined organic layers were dried over magnesium sulphate and evaporated under reduced pressure. The residue was triturated in ether and the crystals obtained were collected on a filter funnel. After drying there were obtained 744 mg (95% of theory) of 2-[4-(4-cyano-benzyloxy)-phenoxy]-N-methyl-acetamide as white crystals; MS: m/e=297 (M+H)$^+$.

EXAMPLE 4

2-[4-(4-Chloro-benzyloxy)-phenoxy]-N-methyl-acetamide

In analogy to the procedure described in Example 3 b), the alkylation of 2-(4-hydroxy-phenoxy)-N-methyl-acetamide [Example 3a)] with 1-bromomethyl-4-chloro-benzene in 2-butanone using potassium carbonate as the base yielded the 2-[4-(4-chloro-benzyloxy)-phenoxy]-N-methyl-acetamide as white crystals; MS: m/e=306 (M+H)$^+$.

EXAMPLE 5

2-[4-(2-Fluoro-benzyloxy)-phenoxy]-N-methyl-acetamide

In analogy to the procedure described in Example 3b), the alkylation of 2-(4-hydroxy-phenoxy)-N-methyl-acetamide [Example 3a)] with 1-bromomethyl-2-fluoro-benzene in 2-butanone using potassium carbonate as the base yielded the 2-[4-(2-fluoro-benzyloxy)-phenoxy]-N-methyl-acetamide as white crystals; MS: m/e=290 (M+H)$^+$.

EXAMPLE 6

2-[4-(3-Fluoro-benzyloxy)-phenoxy]-N-methyl-acetamide

In analogy to the procedure described in Example 3b), the alkylation of 2-(4-hydroxy-phenoxy)-N-methyl-acetamide [Example 3a)] with 1-bromomethyl-3-fluoro-benzene in 2-butanone using potassium carbonate as the base yielded the 2-[4-(3-fluoro-benzyloxy)-phenoxy]-N-methyl-acetamide as white crystals; MS: m/e=290 (M+H)$^+$.

EXAMPLE 7

2-[4-(4-Fluoro-benzyloxy)-phenoxy]-N-methyl-acetamide

A mixture of 500 mg of [4(4-fluoro-benzyloxy)-phenoxy]-acetic acid ethyl ester [Example 1b)] and 2 ml of methylamine (about 8 M in ethanol) was stirred at 80° C. during 18 h. For the working-up, the solution was cooled to room temperature and treated with water. The pure product precipitated and was collected on a filter funnel. After drying there were obtained 398 mg (86% of theory) of 2-[4-(4-fluoro-benzyloxy)-phenoxy]-N-methyl-acetamide as white crystals; MS: m/e=290 (M+H)$^+$.

EXAMPLE 8

2-[4-(4-Fluoro-benzyloxy)-phenoxy]-N,N-dimethyl-acetamide

In analogy to the procedure described in Example 7, the aminolysis of [4-(4-fluoro-benzyloxy)-phenoxy]-acetic acid ethyl ester with dimethylamine yielded the 2-[4-(4-fluoro-benzyloxy)-phenoxy]-N,N-dimethyl-acetamide as white crystals; MS: m/e=304 (M+H)$^+$.

EXAMPLE 9

(RS)-2-(4-Benzyloxy)-phenoxy]-N-methyl-propionamide a) (RS)-2-(4-Benzyloxy-phenoxy)-propionic acid methyl ester In analogy to the procedure described in Example 1b), the alkylation of 4-benzyloxy-phenol [Example 2a)] with methyl (RS)-2-bromopropionate in acetone using cesium carbonate as the base yielded the (RS)-2-(4-Benzyloxy-phenoxy)-propionic acid methyl ester as light yellow oil; MS: m/e=304 (M+NH$_4$)$^+$.

b) (RS)-2-(4-Benzyloxy-phenoxy)-N-methyl-propionamide

In analogy to the procedure described in Example 7, the aminolysis of (RS)-2-(4-benzyloxy)-phenoxy]-N-methyl-propionamide with methylamine yielded the (RS)-2-(4-benzyloxy)-phenoxy]-N-methyl-propionamide as a white solid; MS: m/e=286 (M+H)$^+$.

EXAMPLE 10

(RS)-2-[4-(2-Fluoro-benzyloxy)-phenoxy]-N-methyl-propionamide a) (RS)-2-(4-Hydroxy-phenoxy)-N-methyl-propionamide In analogy to the procedure described in Example 3a), the hydrogenolysis of (RS)-2-(4-benzyloxy)-phenoxy]-N-methyl-propionamide yielded the (RS)-2-(4-hydroxy-phenoxy)-N-methyl-propionamide as white crystals; MS: m/e=194 (M−H)−.

b) (RS)-2-[4-(2-Fluoro-benzyloxy)-phenoxy]-N-methyl-propionamide

In analogy to the procedure described in Example 3b), the alkylation of (RS)-2-(4-hydroxy-phenoxy)-N-methyl-propionamide with 2-fluoro-benzylbromide in 2-butanone using potassium carbonate as the base yielded the (RS)-2-[4-(2-fluoro-benzyloxy)-phenoxy]-N-methyl-propionamide as white crystals; MS: m/e=304 (M+H)$^+$.

EXAMPLE 11

(RS)-2-[4-(3-Fluoro-benzyloxy)-phenoxy]-N-methyl-propionamide

In analogy to the procedure described in Example 3b), the alkylation of (RS)-2-(4-hydroxy-phenoxy)-N-methyl-propionamide with 3-fluoro-benzylbromide in 2-butanone using potassium carbonate as the base yielded the (RS)-2-[4-(3-fluoro-benzyloxy)-phenoxy]-N-methyl-propionamide as a white solid; MS: m/e=304 (M+H)$^+$

EXAMPLE 12

(RS)-2-[4-(3-Chloro-benzyloxy)-phenoxy]-N-methyl-propionamide

In analogy to the procedure described in Example 3b), the alkylation of (RS)-2-(4-hydroxy-phenoxy)-N-methyl-propi onamide with 3-chloro-benzylbromide in 2-butanone using potassium carbonate as the base yielded the (RS)-2-[4-(3-chloro-benzyloxy)-phenoxy]-N-methyl-propionamide as a white solid; MS: m/e=320 (M+H)$^+$.

EXAMPLE 13

(R or S)-2-[4-(3-Chloro-benzyloxy)-phenoxy]-N-methyl-propionamide and (S or R)-2-[4-(3-Chloro-benzyloxy)-phenoxy]-N-methyl-propionamide The separation of 300 mg of the two isomers (RS)-2-[4-(3-chloro-benzyloxy)-phenoxy]-N-methyl-propionamide (Example 12) was performed on a preparative chiral HPLC column (CHIRALPAK® AD, pressure: 20 bar, flow: 35 ml/min) using a 85:15 mixture of n-heptane and ethanol as the eluent. There were obtained 122 mg (41% of theory) of the first eluting isomer (R or S)-2-[4-(3-chloro-benzyloxy)-phenoxy]-N-methyl-propionamide and 860 mg (39% of theory) of the later eluting isomer (S or R)-2-[4-(3-chloro-benzyloxy)-phenoxy]-N-methyl-propionamide, each as a white solid.

EXAMPLE 14

(RS)-2-[4-(4-Cyano-benzyloxy)-phenoxy]-N-methyl-propionamide

In analogy to the procedure described in Example 3b), the alkylation of (RS)-2-(4-hydroxy-phenoxy)-N-methyl-propionamide with 4-bromomethyl-benzonitrile in 2-butanone using potassium carbonate as the base yielded the (RS)-2-[4-(4-cyano-benzyloxy)-phenoxy]-N-methyl-propionamide as a white solid; MS: m/e=311 (M+H)$^+$.

EXAMPLE 15

(RS)-2-(4-Benzyloxy)-phenoxy]-N-methyl-butyramide a) (RS)-2-(4-Benzyloxy-phenoxy)-butyric acid ethyl ester In analogy to the procedure described in Example 1b), the alkylation of 4-benzyloxy-phenol [Example 2a)] with ethyl (RS)-2-bromobutyrate in acetone using cesium carbonate as the base yielded the (RS)-2-(4-benzyloxy-phenoxy)-butyric acid ethyl ester as a brown oil; MS: m/e=314 (M)$^+$.

b) (RS)-2-(4-Benzyloxy-phenoxy]-N-methyl-butyramide

In analogy to the procedure described in Example 7, the aminolysis of the (RS)-2-(4-benzyloxy-phenoxy)-butyric acid ethyl ester with methylamine yielded the (RS)-2-(4-benzyloxy)-phenoxy]-N-methyl-butyramide as a white solid; MS: m/e=300 (M+H)$^+$.

EXAMPLE 16

(RS)-2-[4-(2-Fluoro-benzyloxy)-phenoxy]-N-methyl-butyramide a) (RS)-2-(4-Hydroxy-phenoxy)-N-methyl-butyramide In analogy to the procedure described in Example 3a), the hydrogenolysis of (RS)-2-(4-benzyloxy)-phenoxy]-N-methyl-butyramide yielded the (RS)-2-(4-hydroxy-phenoxy)-N-methyl-butyramide as white crystals; MS: m/e=210 (M+H)$^+$.

b) (RS)-2-[4-(2-Fluoro-benzyloxy)-phenoxy]-N-methyl-butyramide

In analogy to the procedure described in Example 3 b), the alkylation of (RS)-2-(4-hydroxy-phenoxy)-N-methyl-butyramide with 2-fluoro-benzylbromide in 2-butanone using potassium carbonate as the base yielded the (RS)-2-[4-(2-fluoro-benzyloxy)-phenoxy]-N-methyl-butyramide as a white solid; MS: m/e=318 (M+H)$^+$.

EXAMPLE 17

(RS)-2-[4-(3-Fluoro-benzyloxy)-phenoxy]-N-methyl-butyramide

In analogy to the procedure described in Example 3b), the alkylation of (RS)-2-(4-hydroxy-phenoxy)-N-methyl-butyramide with 3-fluoro-benzylbromide in 2-butanone using potassium carbonate as the base yielded the (RS)-2-[4-(3-fluoro-benzyloxy)-phenoxy]-N-methyl-butyramide as a white solid; MS: m/e=318 (M+H)$^+$.

EXAMPLE 18

(RS)-2-[4-(3-Chloro-benzyloxy)-phenoxy]-N-methyl-butyramide

In analogy to the procedure described in Example 3b), the alkylation of (RS)-2-(4-hydroxy-phenoxy)-N-methyl-butyramide with 3-chloro-benzylbromide in 2-butanone using potassium carbonate as the base yielded the (RS)-2-[4-(3-chloro-benzyloxy)-phenoxy]-N-methyl-butyramide as a white solid; MS: m/e=334 (M+H)$^+$.

EXAMPLE 19

(RS)-2-[4-(4-Cyano-benzyloxy)-phenoxy]-N-methyl-butyramide

In analogy to the procedure described in Example 3b), the alkylation of (RS)-2-(4-hydroxy-phenoxy)-N-methyl-butyramide with 4-bromomethyl-benzonitrile in 2-butanone using potassium carbonate as the base yielded the (RS)-2-[4-(4-cyano-benzyloxy)-phenoxy]-N-methyl-butyramide as a white solid; MS: m/e=325 (M+H)$^+$.

EXAMPLE 20

2-(4-Benzyloxy)-phenoxy]-2,N-dimethyl-propionamide

In analogy to the procedure described in Example 7, the aminolysis of the 2-(4-benzyloxy-phenoxy)-2-methyl-propionic acid ethyl ester with methylamine yielded the 2-(4-benzyloxy)-phenoxy]-2,N-dimethyl-propionamide as a white solid; MS: m/e=300 (M+H)$^+$.

EXAMPLE 21

2-[4-(3-Fluoro-benzyloxy)-phenoxy]-2,N-dimethyl-propionamide a) 2-(4-Hydroxy-phenoxy)-2,N-dimethyl-propionamide In analogy to the procedure described in Example 3a), the hydrogenolysis of 2-(4-benzyloxy)-phenoxy]-2,N-dimethyl-propionamide [Example 20] yielded the 2-(4-hydroxy-phenoxy)-2,N-dimethyl-propionamide as a white solid; MS: m/e=209 (M)$^+$.

b) 2-[4-(3-Fluoro-benzyloxy)-phenoxy]-2,N-dimethyl-propionamide

In analogy to the procedure described in Example 3b), the alkylation of 2-(4-hydroxy-phenoxy)-2,N-dimethyl-propionamide with 3-fluoro-benzylbromide in 2-butanone using potassium carbonate as the base yielded the 2-[4-(3-fluoro-benzyloxy)-phenoxy]-2,N-dimethyl-propionamide as an brown oil; MS: m/e=318 $(M+H)^+$.

EXAMPLE 22

2-[4-(3-Chloro-benzyloxy)-phenoxy]-2,N-dimethyl-propionamide

In analogy to the procedure described in Example 3 b), the alkylation of 2-(4-hydroxy-phenoxy)-2,N-dimethyl-propionamide with 3-chloro-benzylbromide in 2-butanone using potassium carbonate as the base yielded the 2-[4-(3-chloro-benzyloxy)-phenoxy]-2,N-dimethyl-propionamide as an brown oil; MS: m/e=334 $(M+H)^+$.

EXAMPLE 23

3-[4-(3-Fluoro-benzyloxy)-phenoxy]-propionamide a) 3-[4-(3-Fluoro-benzyloxy)-phenoxy]-propionic acid methyl ester A solution of 1.5 g of 4-(3-fluoro-benzyloxy)-phenol [prepared in close analogy to the procedure described in Example 1a) for the 4-(3-fluoro-benzyloxy)-phenol] and 1.4 mg of hydroquinone in 5 ml of methyl acrylate was treated with sodium before it was heated to reflux for 7.5 h. For the working-up, the mixture was cooled to room temperature and neutralised with acetic acid. After evaporation under reduced pressure, the residue was dissolved in ether and ethyl acetate, and the resulting solution was extracted three times with water. The organic layer was dried over magnesium sulphate, then evaporated under reduced pressure. The crude product was re-crystallised in a small volume of methanol. There were obtained 1.1 g (54% of theory) of 3-[4-(3-fluoro-benzyloxy)-phenoxy]-propionic acid methyl ester as white crystals; MS: m/e=304 $(M+H)^+$.

b) 3-[4-(3-Fluoro-benzyloxy)-phenoxy]-propionic acid

A solution of 500 mg of 3-[4-(3-fluoro-benzyloxy)-phenoxy]-propionic acid methyl ester in a mixture of 5 ml of tetrahydrofurane and 25 ml of hydrochloric acid (19%) was heated at 70° C. for 7 h. For the working-up, the tetrahydrofurane was evaporated under reduced pressure and the aqueous was extracted three times with 40 ml of ethyl acetate. The combined organic layers were dried over magnesium sulphate and evaporated under reduced pressure. The crude product was triturated in ether and the solid material collected on a filter funnel. After drying there were obtained 114 mg (30% of theory) of 3-[4-(3-fluoro-benzyloxy)-phenoxy]-propionic acid as white crystals.

c) 3-[4-(3-Fluoro-benzyloxy)-phenoxy]-propionamide

A solution of 70 mg of 3-[4-(3-fluoro-benzyloxy)-phenoxy]-propionic acid in 4 ml of dichloromethane (plus 1 drop of N,N-dimethyl-formamide) was cooled to 0° C. and treated with 0.03 ml of oxalyl chloride. Stirring was continued for 1.5 h, thereafter, most of the dichloromethane was evaporated. A solution of 0.5 ml of aqueous ammonium hydroxide (25%) in 1 ml of tetrahydrofurane was prepared and cooled to 0° C. The solution of the acid chloride was added to the aforementioned solution and the mixture was allowed to warm to room temperature while stirring was continued during the weekend. For the working-up, the reaction mixture was evaporated under reduced pressure and the residue triturated in ether delivering 42 mg (60% of theory) of 3-[4-(3-fluoro-benzyloxy)-phenoxy]-propionamide as a white solid; MS: m/e=307 $(M+NH_4)^+$.

EXAMPLE 24

Carbamic acid 2-[4-(3-fluoro-benzyloxy)-phenyl]-ethyl ester a) 2-[4-(3-Fluoro-benzyloxy)-phenyl]-ethanol A mixture of 5.0 g of 2-(4-hydroxyphenyl)-ethanol and 5.0 g of potassium carbonate in 100 ml of acetonitrile was treated dropwise under an atmosphere of argon and at 0° C. with 4.5 ml of 3-fluorobenzylbromide. After complete addition, stirring was continued at 0° C. for 15 minutes, then the reaction mixture was left to warm to room temperature and stirring continued for 18 h. For the working-up, the solvent was evaporated under reduced pressure, thereafter, the residue was dissolved in ethyl acetate and the solution washed with water. The organic layer was dried over magnesium sulphate and evaporated under reduced pressure. For purification, the crude material obtained (10.2 g of a yellow oil) was chromatographed on silica gel using a 95:5-mixture of dichloromethane and methanol as the eluent. After re-crystallisation from a mixture of ether and cyclohexane there were obtained 4.1 g (46% of theory) of 2-[4-(3-fluoro-benzyloxy)-phenyl]-ethanol as a white solid; MS: m/e=247 $(M+H)^+$.

b) Carbamic acid 2-[4-(3-fluoro-benzyloxy)-phenyl]-ethyl ester

Under an argon atmosphere and at room temperature, a suspension of 1.0 g of 2-[4-(3-fluoro-benzyloxy)-phenyl]-ethanol and 0.66 g of potassium isocyanate in 2 ml of benzene was treated dropwise under stirring with 0.62 ml of trifluoroacetic acid. After stirring for 18 h at room temperature, the reaction mixture was diluted with water, then extracted three times with dichloromethane. The combined organic layers were dried over potassium carbonate and evaporated. There were obtained 0.52 g (44% of theory) of carbamic acid 2-[4-(3-fluoro-benzyloxy)-phenyl]-ethyl ester as a white solid; MS: m/e=290 $(M+H)^+$.

EXAMPLE 25

Carbamic acid 4-(3-fluoro-benzyloxy)-benzyl ester a) 4-(3-Fluoro-benzyloxy)-benzaldehyde A mixture of 6.0 g of 4-hydroxy-benzaldehyde and 13.58 g of potassium carbonate in 60 ml of N,N-dimethylformamide was treated dropwise at room temperature with a solution of 11.14 g of 3-fluoro-benzylbromide in 30 ml of N,N-dimethylformamide. After 3 h the reaction mixture was diluted with water and extracted with ether. The organic layer was washed with water, dried over magnesium sulphate and evaporated to yield an oil (9.85 g) which crystallised on standing; MS: m/e=230 $(M)^+$. The crude product was used in the next step without further purification.

b) [4-(3-Fluoro-benzyloxy)-phenyl]-methanol

A solution of 3.79 g of 4-(3-fluoro-benzyloxy)-benzaldehyde in 10 ml of tetrahydrofurane was added dropwise at room temperature to a suspension of 1.25 g of lithium-aluminiumhydride in 40 ml of tetrahydrofurane. After 2 h at room temperature, successively 1.25 ml of water were added dropwise under cooling, then 3.75 ml of a sodium hydroxide solution (1 N), finally, 1.25 ml of water. The mixture was filtered over a layer of Dicalit and the tetrahydrofurane distilled off the solution under reduced pressure. The residual phase was extracted with ethyl acetate, the combined organic layers were dried over magnesium sulphate und evaporated under reduced pressure. The residue was crystallised from a mixture of ether and n-hexane to yield 2.26 g (59% of theory) of [4-(3-fluoro-benzyloxy)-phenyl]-methanol as a white solid; MS: m/e=232 (M)$^+$.

c) Carbamic acid 4-(3-fluoro-benzyloxy)-benzyl ester

In analogy to the procedure described in Example 24 b), the reaction of [4-(3-fluoro-benzyloxy)-phenyl]-methanol with potassium isocyanate and trifluoroacetic acid in benzene yielded the carbamic acid 4-(3-fluoro-benzyloxy)-benzyl ester as a white solid; MS: m/e=293 (M+NH$_4$)$^+$.

EXAMPLE 26

Methyl-carbamic acid 4-(3-fluoro-benzyloxy)-benzyl ester

In a sealed glass tube, a solution of 1.0 g of [4-(3-fluoro-benzyloxy)-phenyl]-methanol [Example 25b)], 0.03 ml of triethylamine and 0.245 g of methyl isocyanate in 40 ml of dichloromethane was heated at 40° C. for 3 d. At that time a transformation rate of 50% was reached, determined by NMR. For the working-up, the reaction mixture was cooled and evaporated. The residue was dissolved in 2 ml of pyridine and 1 ml of acetic acid anhydride and the solution stirred at room temperature for 3 h. Thereafter, the mixture was evaporated under reduced pressure. For purification, the crude material obtained was chromatographed on silica gel using a 2:1-mixture of heptane and ethyl acetate as the eluent. There were obtained 580 mg (47% of theory) of methyl-carbamic acid 4-(3-fluoro-benzyloxy)-benzyl ester as a white solid; MS: m/e=289 (M)$^+$.

EXAMPLE 27

2-[4-(3-Fluoro-benzyloxy)-benzyloxy]-acetamide

A solution of 500 mg of [4-(3-fluoro-benzyloxy)-phenyl]-methanol [Example 25b)] in 10 ml of tetrahydrofurane was treated at room temperature with 57 mg of sodium hydride (55% dispersion in oil) and stirred for 1 h. Thereafter, 183 mg of chloroacetamide were added and the mixture was heated to reflux for 48 h. For the working-up, the cooled mixture was treated with water and extracted with ethyl acetate. The organic layer was dried over magnesium sulphate and evaporated under reduced pressure. For purification, the crude material obtained was chromatographed on silica gel using a gradient of dichloromethane to a 4:1-mixture-mixture of dichloromethane and methanol as the eluent. After crystallisation from ether, there were obtained 29 mg (5% of theory) of 2-[4-(3-fluoro-benzyloxy)-benzyloxy]-acetamide as a white solid; MS: m/e=307 (M+NH$_4$)$^+$.

EXAMPLE A

Tablets of the following composition are produced in a conventional manner:

|  | mg/Tablet |
| --- | --- |
| Active ingredient | 100 |
| Powdered.lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
| --- | --- |
| Active ingredient | 200 |
| Powdered.lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
| --- | --- |
| Active ingredient | 50 |
| Crystalline.lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

EXAMPLE D

An injection solution may have the following composition and is manufactured in usual manner:

| Active substance | 1.0 mg |
| --- | --- |
| 1 N HCl | 20.0 µl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

The invention claimed is:

1. A compound of the formula

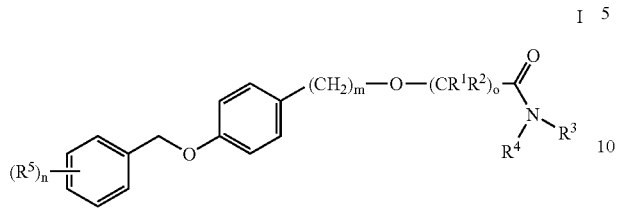

wherein
$R^1$ and $R^2$ are each independently hydrogen or $C_1$-$C_6$-alkyl;
$R^3$ and $R^4$ are each independently hydrogen or $C_1$-$C_6$-alkyl;
$R^5$ is CN, $(C_1$-$C_6)$-alkyl or $(C_1$-$C_6)$-alkoxy; and
n is 1 or 2; and
m and o are each independently 0, 1 or 2;
or a pharmaceutically acceptable salt thereof.

2. A compound of formula I according to claim 1, wherein o is 1 and m is 0.

3. A compound selected from the group consisting of
3-[4-(3-fluoro-benzyloxy)-phenoxy]-propionamide
carbamic acid 2-[4-(3-fluoro-benzyloxy)-phenyl]-ethyl ester
methyl-carbamic acid 4-(3-fluoro-benzloxy)-benzyl ester
2-[4-(4-chloro-benzyloxy)-phenoxy]-N-methyl-acetamide,
2-[4-(2-fluoro-benzyloxy)-phenoxy]-N-methyl-acetamide,
2-[4-(3-fluoro-benzyloxy)-phenoxy]-N-methyl-acetamide,
2-[4-(4-fluoro-benzyloxy)-phenoxy]-N-methyl-acetamide,
(RS)-2-[4-(3-fluoro-benzyloxy)-phenoxy]-N-methyl-propionamide
(RS)-2-[4-(3-chloro-benzyloxy)-phenoxy]-N-methyl-propionamide
(S or R)-2-[4-(3-chloro-benzyloxy)-phenoxy]-N-methyl-propionamide,
(RS)-2-[4-(3-fluoro-benzyloxy)-phenoxy]-N-methyl-propionamide,
(RS)-2-[4-(3-chloro-benzyloxy)-phenoxy]-N-methyl-butyramide.

4. A compound of formula I according to claim 1, wherein o is 2 and m is 0.

5. A compound of formula I according to claim 1, wherein o is 0 and m is 2.

6. A compound of formula I according to claim 1, wherein o is 0 and m is 1.

7. A compound of formula I according to claim 1, wherein n is 1.

8. A compound of formula I according to claim 1, wherein $R^1$ and $R^2$ are both hydrogen.

9. A compound of formula I according to claim 1, wherein $R^1$ is $C_1$-$C_6$-alkyl.

10. A compound of formula I according to claim 9, wherein $R^1$ is $CH_3$ or $CH_2CH_3$.

11. A compound of formula I according to claim 9, wherein $R^2$ is hydrogen.

12. A compound of formula I according to claim 1, wherein $R^1$ and $R^2$ are each independently $C_1$-$C_6$-alkyl.

13. A pharmaceutical composition comprising a compound of the formula

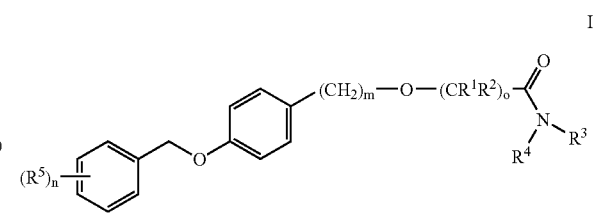

wherein
$R^1$ and $R^2$ are each independently hydrogen or $C_1$-$C_6$-alkyl;
$R^3$ and $R^4$ are each independently hydrogen or $C_1$-$C_6$-alkyl;
$R^5$ is CN, $(C_1$-$C_6)$-alkyl or $(C_1$-$C_6)$-alkoxy; and
n is 1 or 2; and
m and o are each independently 0, 1 or 2;
or a pharmaceutically acceptable salt thereof
and a pharmaceutically acceptable carrier.

14. A process for preparation of compounds of formula I

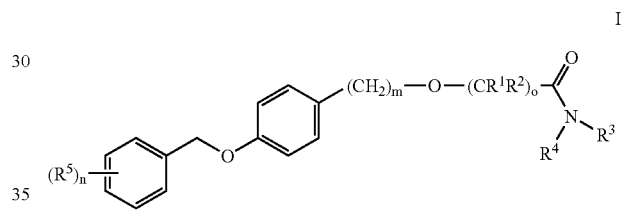

wherein
$R^1$ and $R^2$ are each independently hydrogen or $C_1$-$C_6$-alkyl;
$R^3$ and $R^4$ are each independently hydrogen or $C_1$-$C_6$-alkyl;
$R^5$ is CN, $(C_1$-$C_6)$ alkoxy; and
n is 1 or 2;
m and o are 0, 1 or 2;
or a pharmaceutically acceptable salt thereof, which process comprises one of the following process
a) reacting a compound of formula

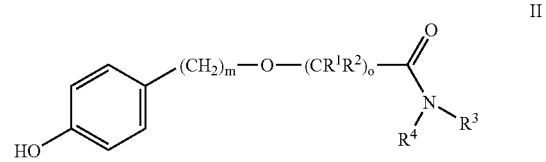

with a compound of formula

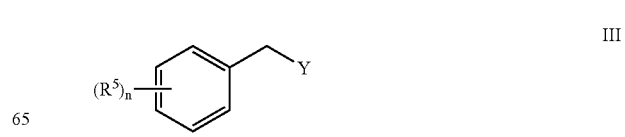

wherein Y is a leaving group, to obtain a compound of formula

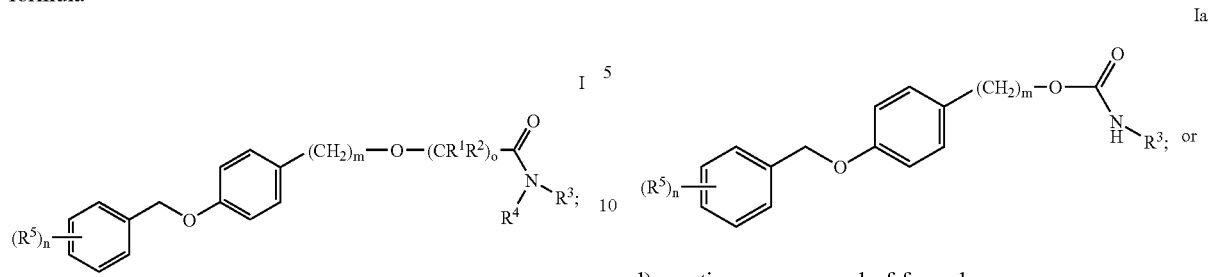

I b) reacting a compound of formula

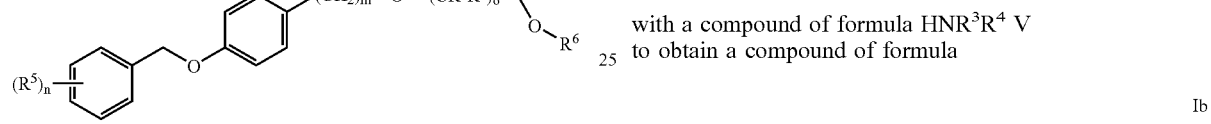

IV wherein $R^6$ is $C_1$-$C_6$-alkyl, with an amine of formula

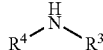

V to obtain a compound of formula

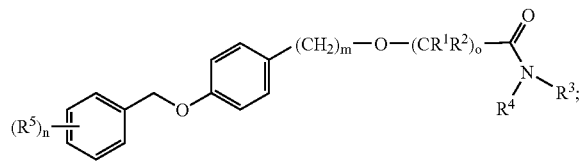

I c) reacting a compound of formula

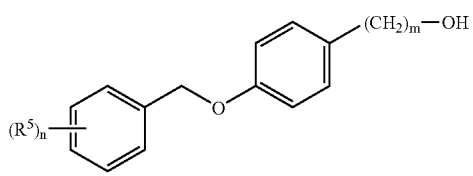

VI with KOCN or with $R^3$—N=C=O

VII to obtain a compound of formula

Ia d) reacting a compound of formula

VIII with a compound of formula $HNR^3R^4$ V to obtain a compound of formula

Ib

15. A compound selected from the group consisting of
2-[4-(4-cyano-benzyloxy)-phenoxy]-N-methyl-acetamide,
(RS)-2-[4-(4-cyano-benzyloxy)-phenoxy]-N-methyl-propionamide, and
(RS)-2-[4-(4-cyano-benzyloxy)-phenoxy]-N-methyl-butyramide.

16. A pharmaceutical composition comprising a compound selected from the group consisting of
2-[4-(4-chloro-benzyloxy)-phenoxy]-N-methyl-acetamide,
2-[4-(2-fluoro-benzyloxy)-phenoxy]-N-methyl-acetamide,
2-[4-(3-fluoro-benzyloxy)-phenoxy]-N-methyl-acetamide,
2-[4-(4-fluoro-benzyloxy)-phenoxy]-N-methyl-acetamide,
(RS)-2-[4-(3-fluoro-benzyloxy)-phenoxy]-N-methyl-propionamide
(RS)-2-[4-(3-chloro-benzyloxy)-phenoxy]-N-methyl-propionamide
(S or R)-2-[4-(3-chloro-benzyloxy)-phenoxy]-N-methyl-propionamide,
(RS)-2-[4-(3-fluoro-benzyloxy)-phenoxy]-N-methyl-butyramide, and
(RS)-2-[4-(3-chloro-benzyloxy)-phenoxy]-N-methyl-butyramide.

17. A pharmaceutical composition comprising a compound selected from the group consisting of
2-[4-(4-cyano-benzyloxy)-phenoxy]-N-methyl-acetamide,
(RS)-2-[4-(4-cyano-benzyloxy)-phenoxy]-N-methyl-propionamide, and
(RS)-2-[4-(4-cyano-benzyloxy)-phenoxy]-N-methyl-butyramide.

* * * * *

UNITED STATES PATENT AND TRADEMARK OFFICE
CERTIFICATE OF CORRECTION

| | | |
|---|---|---|
| PATENT NO. | : 7,253,318 B2 | |
| APPLICATION NO. | : 11/156417 | |
| DATED | : August 7, 2007 | |
| INVENTOR(S) | : Jolidon et al. | |

It is certified that error appears in the above-identified patent and that said Letters Patent is hereby corrected as shown below:

TITLE PAGE:

Item [75] The Assignee information reads "Hoffman-La Roche Inc., Nutley, NJ (US)".
The Assignee information should read -- Hoffmann-La Roche Inc., Nutley, NJ (US) --.

Signed and Sealed this

Fourth Day of December, 2007

JON W. DUDAS
*Director of the United States Patent and Trademark Office*